United States Patent [19]
Cook et al.

[11] Patent Number: 6,049,729
[45] Date of Patent: Apr. 11, 2000

[54] DOSE MASKING FEATURE FOR BNCT RADIOTHERAPY PLANNING

[75] Inventors: Jeremy L. Cook, Greeley, Colo.;
Daniel E. Wessol, Bozeman, Mont.;
Floyd J. Wheeler, Idaho Falls, Id.

[73] Assignee: Bechtel BWXT Idaho, LLC, Idaho Falls, Id.

[21] Appl. No.: 08/956,811

[22] Filed: Oct. 23, 1997

[51] Int. Cl.[7] .................................................. A61B 5/05
[52] U.S. Cl. ............................................................ 600/407
[58] Field of Search .................................. 600/423, 1–3; 378/65, 63; 434/262

[56] References Cited

U.S. PATENT DOCUMENTS

| | | | |
|---|---|---|---|
| 3,987,281 | 10/1976 | Hodes | 600/427 |
| 4,455,609 | 6/1984 | Inamura et al. | 364/414 |
| 4,998,268 | 3/1991 | Winter | 378/63 |
| 5,341,292 | 8/1994 | Zamenhof | 363/414 |

Primary Examiner—Marvin M. Lateef
Assistant Examiner—Maulin Patel
Attorney, Agent, or Firm—Thorpe North & Western

[57] ABSTRACT

A system for displaying an accurate model of isodoses to be used in radiotherapy so that appropriate planning can be performed prior to actual treatment on a patient. The nature of the simulation of the radiotherapy planning for BNCT and Fast Neutron Therapy, etc., requires that the doses be computed in the entire volume. The "entire volume" includes the patient and beam geometries as well as the air spaces in between. Isodoses derived from the computed doses will therefore extend into the air regions between the patient and beam geometries and thus depict the unrealistic possibility that radiation deposition occurs in regions containing no physical media. This problem is solved by computing the doses for the entire geometry and then masking the physical and air regions along with the isodose contours superimposed over the patient image at the corresponding plane. The user is thus able to mask out (remove) the contour lines from the unwanted areas of the image by selecting the appropriate contour masking region from the raster image.

21 Claims, 4 Drawing Sheets

DOSE MASKING FEATURE FOR BNCT RADIOTHERAPY PLANNING

CONTRACTUAL ORIGIN OF THE INVENTION

The United States has rights in this invention pursuant to Contract No. DE-AC07-941D13223 between the U.S. Department of Energy and Lockheed Martin Idaho Technologies Company.

BACKGROUND OF THE INVENTION

1. Field of the Invention

This invention relates to radiotherapy planning for Boron Neutron Capture Therapy (BNCT). More specifically, the present invention relates to a method for improving the simulation and display of BNCT isodoses superimposed upon the anatomical features of a patient that are to receive BNCT treatment.

2. Background Art

Application of neutrons for radiotherapy of cancer has been a subject of considerable clinical and research interest since the discovery of the neutron by Chadwick in 1932. Fast neutron radiotherapy was first used by Robert Stone in the Lawrence Berkeley Laboratory in 1938. This technology has evolved over the years to the point where it is now a very viable method for treating inoperable salivary gland tumors. On the basis of recent research data such technology also is emerging as a promising alternative for treatment for prostate cancer, some lung tumors, and certain other malignancies as well.

Neutron capture therapy (NCT), a somewhat different form of neutron-based therapy, was proposed in the mid 1930s and, despite some notable failures in early U.S. trials, has attracted a great deal of renewed research interest lately. This interest is due to significant improvements in radiobiological knowledge.

The basic physical processes involved in fast neutron therapy and neutron capture therapy differ in several respects. In fast neutron therapy, neutrons having relatively high energy (approximately 30–50 MeV) are generated by a suitable neutron source and used directly for irradiation of the treatment volume, just as is done with standard photon (x-ray) therapy. In neutron capture therapy, a neutron capture agent is injected into the patient and is selectively taken into the malignant tissue. The administration of a pharmaceutical containing the neutron capture agent is preferably direct administration into the bloodstream of the patient. At an appropriate time after administration of the neutron capture agent, the treatment volume (i.e., the anatomical structure to be treated) is exposed to a field of thermal neutrons produced by application of an external neutron beam. Because boron-10 is commonly used as the capture agent, the technology has come to be known as boron neutron capture therapy, or BNCT.

The thermal neutrons interact with the boron-10, which has a very high capture cross-section in the thermal energy range. Ideally, the boron-10 is present only in the malignant cells so that boron-neutron interactions will occur only in malignant cells. Each boron-neutron interaction produces an alpha particle and a lithium ion. These highly-energetic charged particles deposit their energy within a geometric volume that is comparable to the size of the malignant cell. Thus, boron-neutron interaction provides a high probability of cell inactivation by direct DNA damage.

Because boron is ideally taken up only in the malignant cells, the NCT process offers the possibility of highly selective destruction of malignant tissue while causing minimal damage to the normal tissue disposed adjacent to the tumor. When boron-10 is taken up in the malignant cells only, the separation between normal and malignant tissue occurs on a cellular-level basis—thereby providing considerable accuracy. In addition, the neutron sources used for NCT are, themselves, designed to produce a minimal level of damage to normal tissue which has not received the neutron capture agent.

When BNCT is administered as a primary therapy, an epithermal-neutron beam (neutrons having energies in the range of 1 eV to 10 keV) is used to produce the required thermal neutron flux at depth. This is because these somewhat higher-energy neutrons will penetrate deeper into the irradiation volume before thermalizing. Although the neutrons penetrate deeper, they are still not of sufficient energy to inflict unacceptable damage to intervening normal tissue.

A third form of neutron therapy is also a subject of current research interest. The third form of neutron therapy is basically a hybrid that combines the features of fast neutron therapy and NCT. In this type of radiotherapy, a neutron capture agent is introduced into a patient—preferably into the malignant tissue only. This treatment is prior to the administration of standard fast neutron therapy. Because a small fraction of the neutrons in fast neutron therapy will be thermalized in the irradiation volume, it is possible to obtain a small incremental absorbed dose from the neutron capture interactions that result. Thus, based on current radiobiological research, improved tumor control appears to be likely when using the augmentation concept.

One significant problem with the various neutron therapy systems is that they are usually located only at major research centers because they are physically complex, bulky, expensive to acquire and require high-level operating staffs to maintain. In general these systems are not well suited for wide-spread, practical, clinical deployment.

This disadvantage is compounded by the fact that in BNCT and other neutron therapy systems detailed planning calculations are necessary to optimize the treatment for each individual patient. Careful planning permit the delivery of the highest possible therapeutic radiation dose to the target tissue while maintaining the surrounding healthy tissue at or below tolerance. However, extensive planning can limit the number of patients which can be properly treated using neutron therapy equipment. Thus, in recent years significant efforts have been made to develop modern computational methods and software for use in BNCT treatment planning.

One such treatment planning system for BNCT has been developed by the New England Medical Center Hospitals. This system is described in U.S. Pat. No. 5,341,292 (Zamenhof), entitled Monte Carlo Based Treatment Planning for Neutron Capture Therapy. The Zamenhof system displays a patient image superimposed with isodose contour lines. To obtain a patient image superimposed with isodose contour lines, the system must process both a physical distribution and a biological distribution. Processing both the physical and biological distributions each time a user desires to view isodose contours on a patient image is inefficient and time consuming.

In addition, the Zamenhof system uses an undesirable method to eliminate unwanted isodose contours. Isodose contours appear everywhere that they are computed to appear—even in areas of the display that do not have a patient image. The isodose contours that appear outside the patient image are undesirable. To get rid of these contour lines, the Zamenhof method sets computed isodose values outside the patient image to zero. Zamenhof, Col. 2, lines 2–4. Setting the computed isodose values to zero in the air regions outside the patient image causes the isodose curves to have unrealistic dropouts near the margins of the patient image. These dropouts are sharp and cause a general distortion throughout the isodose curves.

Other treatment planning systems consider the isodose contours to consist of one component and present the contours on top of a medical image or graphical, visual representation of anatomical features. Although these systems increase the speed of treatment planning, they are not as accurate as desired.

Thus, there is a need for a method for treatment planning that provides for isodose contour line displays superimposed over a patient image, while eliminating the contour lines in areas not of concern to the user. Such a system should be easy to use and enable more efficient treatment planning.

OBJECTS AND SUMMARY OF THE INVENTION

It is an object of the present invention to provide a system for displaying an accurate model of isodoses used in BNCT and related types of radiotherapy.

It is another object of the present invention to provide such a system which enables a graphic display of an image of a desired anatomical feature of a patient with isodose contours superimposed thereon to reflect radiotherapy treatment.

It is yet another object of the present invention to enable the user to select what portion of the anatomical feature and the surrounding area is displayed.

The present invention involves a method and a system, wherein the method involves processing signals to generate a visual display of a desired anatomical feature. Isodose contour lines representative of the radiotherapy are superimposed over the anatomical feature displayed so as to indicate the effect of the neutron therapy on the patient. A raster image is then superimposed on the anatomical feature of the patient and isodose contour lines to selectively mask the contour lines in areas other than the desired anatomical feature so that isodose contour lines that are not wanted will not appear. What determines which isodose contour lines are undesired and will not appear can be controlled by the user to thereby facilitate planing of the radiotherapy.

In accordance with another aspect of the present invention, the system includes a processor, typically a computer, connected to a display. The processor is programmed to process information supplied by the user to develop a graphical representation of the anatomical feature undergoing treatment, to develop a visual representation of the neutron propagation (contour lines) and to develop a raster image which selectively masks the undesired contour lines.

The present invention provides a convenient way for the user to remove the isodose curves from areas of the display that isodose curves are not wanted. Removing these isodose curves facilitates the envisioning of the computed dose information. The quicker comprehension of dose information gives this invention numerous advantages. Primarily, the invention will reduce the amount of clinical staff time spent developing a specific treatment plan. This, in turn, will increase patient throughput. An increased patient throughput allows for more efficient usage of expensive resources and thereby makes radiotherapy more cost efficient than in the past. Other advantages will become apparent from the detailed description and the claims.

In accordance with one aspect of the invention, the steps of providing a visual representation of the anatomical feature, superimposing an isodose pattern of contour lines generated by processing of the weighting values and applying a raster image to selectively mask contour lines outside a desired area is repeated until a desired contour line pattern is viewed on the display. With the desired contour line pattern present on the screen, the operator may then quickly determine the proper radiotherapy dose.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION OF THE PREFERRED EMBODIMENTS

Figure 1:
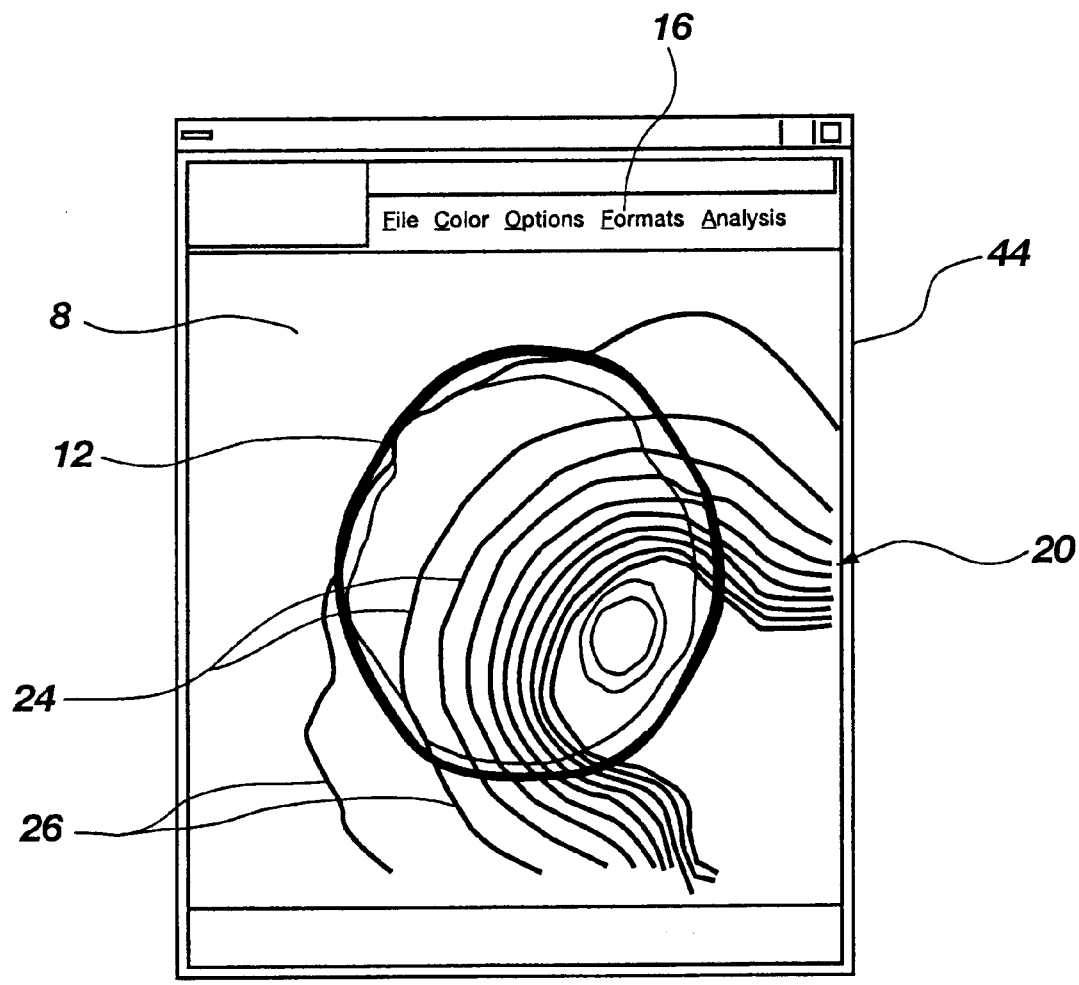
FIG. 1 is an example of a view of a patient image superimposed with completely unmasked isodose contour lines to demonstrate the lack of clarity of images used in radiotherapy treatment planning.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

The method for displaying an accurate model of isodose contour lines from Boron Neutron Capture Therapy (BNCT) or other radiotherapy includes a number of steps. Following these steps is necessary to provide accurate and efficient planning of the radiotherapy. The method of the present invention is useful because if the steps are followed properly, the adverse affects of BNCT radiotherapy on a patient's normal tissue can be minimized, while at the same time improving planning time and patient throughput.

The first step of the method is obtaining a plurality of weighting values (or conversion factors) for at least one component of BNCT radiotherapy, etc. As stated above, BNCT radiotherapy usually involves a number of components which must be processed to provide an effective radiotherapy treatment plan. Each component has a weighting factor that affects the radiotherapy treatment of the total combination of components. The weighting values can be individually altered to change the radiotherapy treatment that is to be applied. To begin BNCT treatment planning, each BNCT component has weighting values assigned. The process for assigning the weighting values will be known to those skilled in the art of BNCT radiotherapy.

Weighting values, or conversion factors are empirical values determined through experimentation. Those skilled in the art are not in complete agreement on the entire group of weighting values. Thus, it is important to have a simulation method which enables rapid, accurate reproductions of the dose distributions. For this reason, it is helpful to have a table of weighting values and a selection tool to avoid tedious, error prone manual entry from a keyboard or other input device.

Once a particular weighting value is selected from a table or some other source, it is entered into a processor, typically by a means such as a keyboard. For this reason, a table of different weighting values is helpful. If the person entering the values is skilled in the art, common results of treatment with the given weighting values is also obtained.

Another way to assign weighting values is through a radiation transport module. Radiation transport modules are common and, in light of the present disclosure, those skilled in the art will recognize how to input the information obtainable therefrom to achieve the desirable results provided by the present invention. Most typically, the radiation transport module will have an output that is coupled to a computer. The computer processes the weighting values and other factors and generates signals which produce a visual representation on a display.

As a first step, the processor generates signals which are converted by the display into a graphical representation of an anatomical feature to be treated with the radiotherapy. Due to problems associated with operating on many tumors in the head, a cross-sectional view of a skull is a common image.

The next step in the method is computing at least one radiotherapy dose from the plurality of weighting values. The BNCT or other radiotherapy dose is computed based on the entire treatment volume. The treatment volume includes three areas: (a) the area of patient anatomy that is to receive radiotherapy, (b) the area including beam geometries, and (c) the area that includes air spaces in between the patient anatomy and the beam geometries. Thus, for example, the BNCT doses are computed for BNCT treatment planning regardless of the extra space involved in the treatment volume.

Once a dose is computed, isodoses can be derived by using currently available software on a conventional computer or other processor. The isodose is the actual dose that is used to administer the radiotherapy. The isodose is not easily visualized, so the next step is directed toward a method for viewing the isodose.

Viewing the isodose is accomplished by displaying contour lines to represent the derived isodoses. The contour lines extend through the entire treatment volume—i.e. the treatment volume and the surrounding environment. FIG. 1 shows a display screen 8 having an anatomical feature 12 displayed thereon. Preferably, the display screen 8 will serve as a graphical user interface and provide a tool bar 16 or other mechanism for selecting the information shown.

The anatomical feature 12 has contour lines 20 representing isodoses superimposed on the anatomical feature. As is apparent from FIG. 1, the isodose model shows contour line portions 24 which are superimposed on the anatomical feature 12, as well as contour line portions 26 that extend beyond the area of patient anatomy (hereinafter referred to as "extraphysical") and across air spaces in between the patient anatomy and the beam geometry. The contour line portions 24 are accurate as far as the patient anatomy is concerned, but with regard to the air spaces and beam geometries, the contour line portions 26 are inaccurate.

As was mentioned in the background section, methods have been developed to eliminate the extraphysical contour line portions 26. However, these methods often unnecessarily skewed the contour line portions 24 superimposed on the anatomical feature 12. Thus, as discussed above, there is a need to effectively eliminate the isodose contour line portions 26 that are inaccurately portrayed in the figure.

Figure 2:
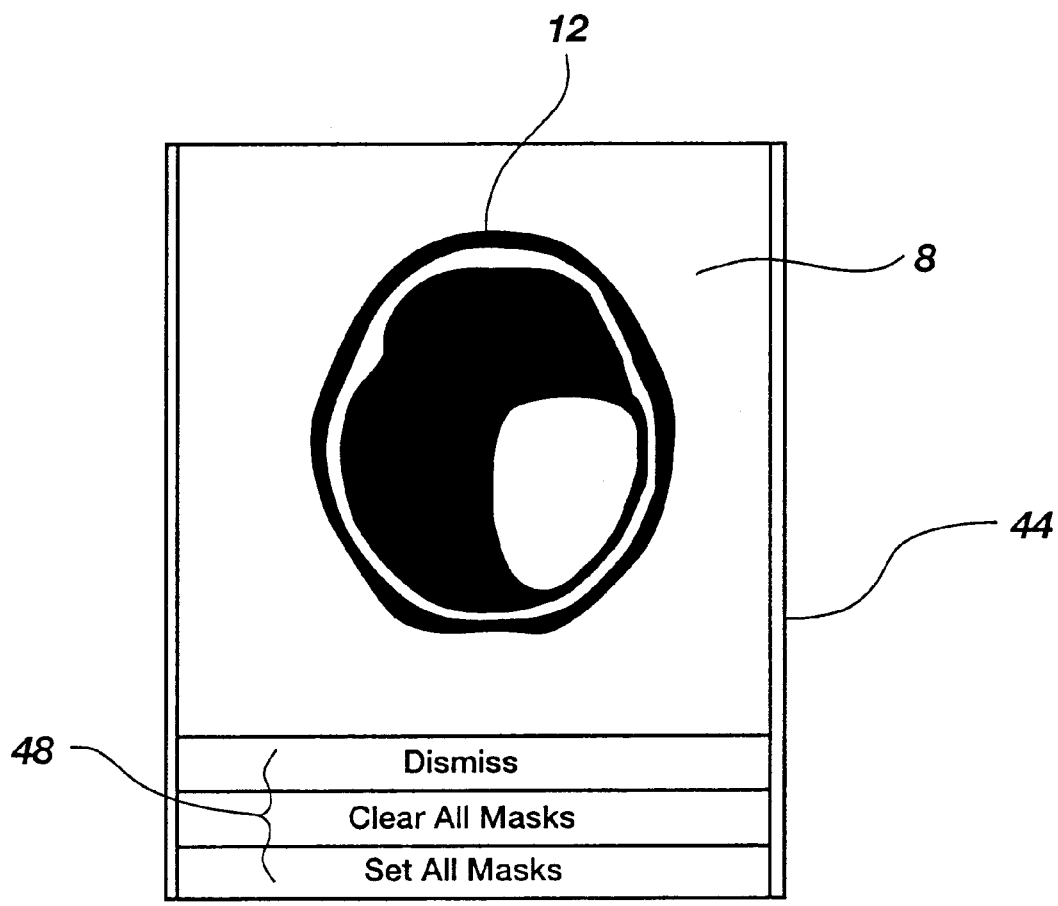
FIG. 2 is a view of the contour masking tool showing a raster image of a model of anatomical features and selections for a user to control the application of the raster image.

This step is accomplished by providing a user with a raster image, generally indicated at 44, which is shown in FIG. 2 on the display screen 8 and shown in FIG. 2. Because the display screen 8 will typically form part of a graphical user interface, a menu of options 48 or some other input arrangement will typically be provided.

The raster image 44 is configured for selectively mask out areas of unwanted isodose contour lines or line portions, such as the extraphysical contour line portions 26 of FIG. 1. The raster image 44 is an image that highlights a particular portion of the display. The highlighted portion of the display is the only portion of the display that is visible to a viewer. Thus, those areas of the display that are highlighted by the raster image will be the only areas of the display that are illuminated in the completed model of isodoses for use in BNCT or other radiotherapy and only contour line portions disposed within the highlighted area will be visible.

Figure 3:
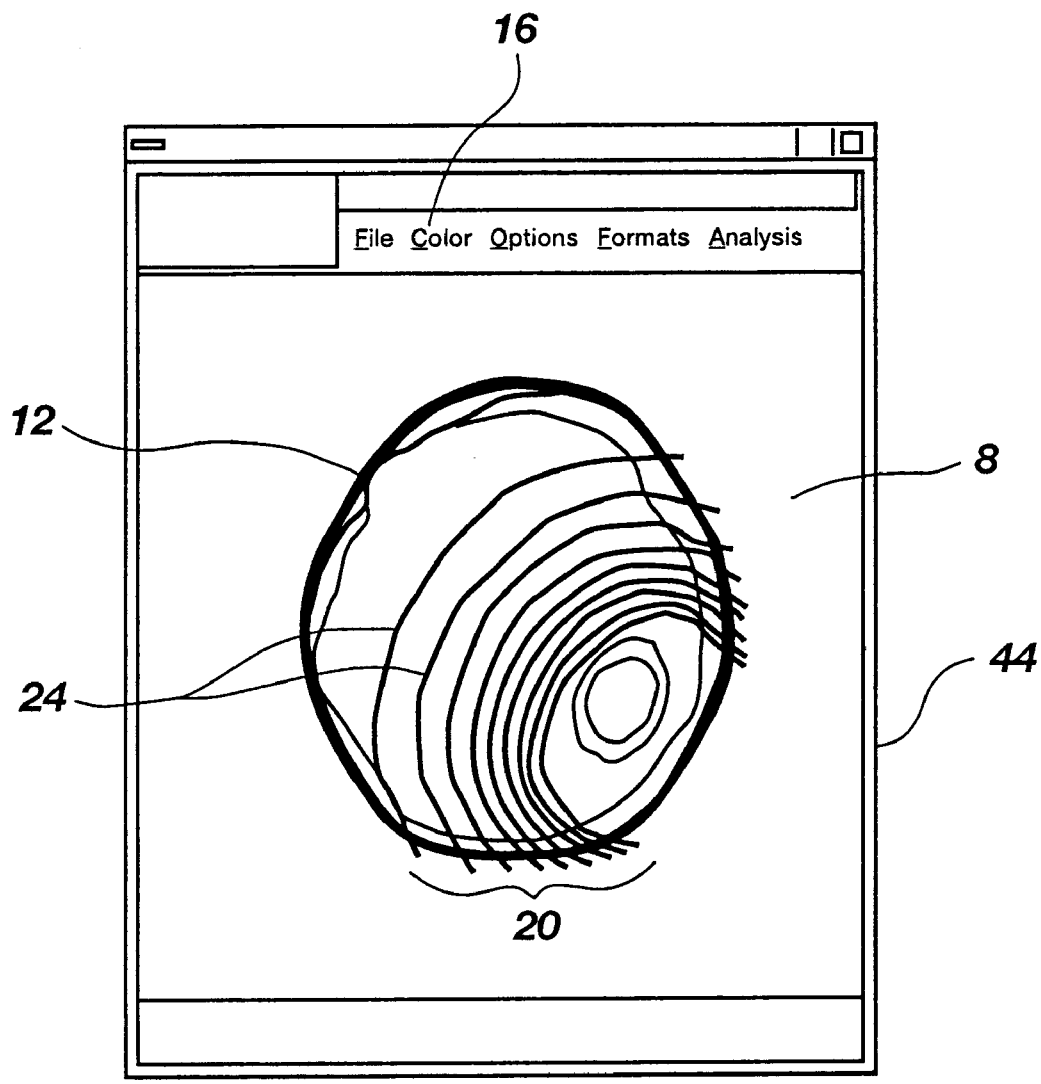
FIG. 3 is an example of a patient treatment volume with isodose contour lines superimposed over the patient treatment volume and the extraphysical isodose contour lines being masked out by the raster image.

The final step of the method is to superimpose the raster image 44 on the anatomical feature 12 and the contour lines 20 to selectively mask out the areas of unwanted isodose contour lines or line portions. In this way, the model will display a patient image superimposed with realistic isodose contour lines or line portions as is shown in FIG. 3. The isodose contour line portions 24 do not extend beyond the image of the anatomical feature 12 and into the air spaces about the anatomical feature. Additionally, no processing has occurred with respect to the contour line portions 24 which would cause the contour lines 24 on the anatomical feature 12 to be skewed or otherwise inaccurate. Thus, an accurate model of isodoses in the radiotherapy appears on the display. This allows BNCT treatment planning to be accomplished with greater quality.

To accomplish the advantages of the present invention, little additional hardware is required. All of the calculations, processing and human perceptible display can occur on a conventional computer. Currently available programs permit the generation of the graphical image of the anatomical feature 12 and the contour lines 20 of the radiotherapy isodoses by the use of the weighting values discussed above. In light of the present disclosure, those skilled in the art will be able to find or prepare software designed to generate a raster image. By combining the respective elements, the significant advantages of the present invention can be achieved.

The software or firmware on the general purpose computer or other processor takes the computed dose and uses it to derive isodoses. In other words, the software processes the weighting values to derive the isodoses from the computed dose. The software on the processor then processes the derived isodoses and displays the isodose contour lines in a manner based on the derived isodoses.

The software on the processor is programmed such that it provides a user with a raster image to selectively mask out areas of unwanted isodose contour lines. While the raster image typically corresponds to the patient image on the display, the raster image could be modified to consider only portions of the anatomical feature depicted on the display. Thus, the patient image shows the anatomical features of a patient that are to be treated and an accurate representation of the contour lines.

The present invention can also be viewed as a system for displaying an accurate model of isodoses used in Boron Neutron Capture Therapy (BNCT) and other radiotherapy planning. BNCT radiotherapy uses a complex arrangement of dose components. Each dose component has a specific weighting value. The present invention assists a BNCT administrator in viewing the predicted treatment outcome of the various combinations of dose components and weighting values. The end goal of this method is to find weighting values of BNCT treatment that will have the greatest effect on the malignant tissue, while having the least detrimental effect on the normal tissue of the patient being treated.

Figure 4:
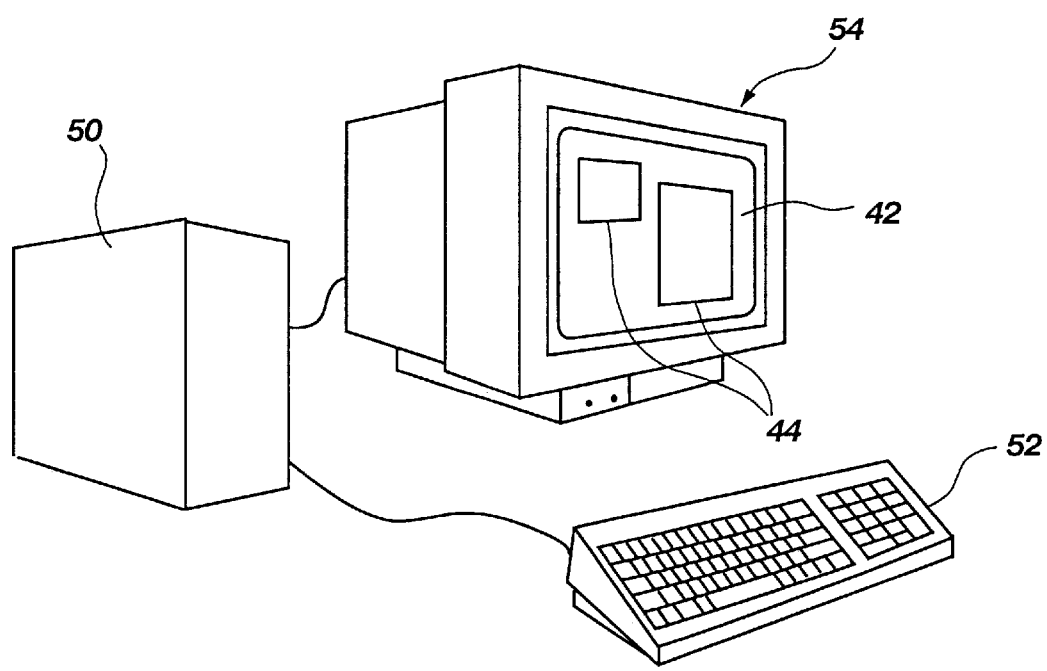
FIG. 4 is a perspective view of a processor and a display device forming a graphical user interface.

As shown in FIG. 4, the system for displaying an accurate model of isodoses used in BNCT treatment uses a processor 50 in the form of a conventional computer. The processor receives input from a keyboard 52, or some other mechanism for imputing data regarding the weighting values or other variable to be applied.

The processor utilizes the information provided regarding the anatomical feature to be treated, the isodose to be applied, and the desired area of viewing to generate signals which are conveyed to a display device, such as a monitor 54. The display device converts the signals from the processor into a graphical representation of the anatomical feature, a contour line pattern superimposed on the anatomical feature indicative of the isodoses, and a raster image which may be superimposed on the anatomical feature and the contour lines to provide an image of the contour lines superimposed only a desired portion of the anatomical feature and not over the extraphysical area.

By layering the graphical representations of the anatomical feature (FIG. 1), the superimposed contour lines (FIG. 1) and the raster image (FIG. 2), the view provided to the user is that of the anatomical feature 12, or desired portion thereof, and only the relevant contour lines. Because no attempts have been made to change the parameters to remove the extraphysical contour line portions and the isodose image (FIG. 1) is computed for the entire treatment volume, the portions of the contour lines superimposed on the anatomical feature are accurate. Thus, by masking, accuracy may be maintained while still providing a convenient visualization tool.

The above variations are not inclusive. They are only examples of the preferred embodiments. It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

We claim:

1. A method for providing an improved visual representation of radiotherapy isodoses applied to an anatomical feature, the method comprising:
   (a) displaying, on a display screen a visual representation of an anatomical feature to undergo radiotherapy;
   (b) generating a visual representation of an isodose pattern in the form of a plurality of contour lines, which extend beyond the visual representation of the anatomical feature, indicative of a radiotherapy dose;
   (c) superimposing, on the display screen, the contour lines of the isodose pattern over the visual representation of the anatomical feature; and
   (d) masking the contour lines that extend beyond the visual representation of the anatomical feature to remove the contour lines from the visual display prior to undergoing a therapy session.

2. The method according to claim 1, wherein the method comprises generating a visual representation of a treatment volume having contour lines as shown in the display, the treatment volume including the anatomical feature and an extraphysical area, and masking the contour lines present in said extraphysical area of the treatment volume.

3. The method according to claim 2, wherein the method comprises generating a raster image to mask the contour lines extending beyond the visual representation of the anatomical feature into the extraphysical area of the treatment volume as shown in the display.

4. The method according to claim 1, wherein step (d) comprises, more specifically, generating a visual representation of the treatment volume as shown in the display where contour lines are to be removed from the visual display.

5. The method according to claim 1, wherein step (d) comprises, more specifically, generating a raster image for highlighting a desired area including at least a portion of the visual representation of the anatomical feature; and superimposing the raster image over the visual representation of the anatomical feature and over the isodose contour lines to selectively mask isodose contour lines outside the desired area.

6. The method according to claim 5, wherein the method comprises, more specifically, selecting as the desired area the entire anatomical feature displayed.

7. The method according to claim 5, wherein the method comprises, more specifically, selecting the desired area to mask extraphysical portions of the contour lines.

8. A system for simulating radiotherapy doses to provide a desired dosing plan, the system comprising:
   (a) display means for producing a visual display;
   (b) means for developing a visual representation of an anatomical feature to be subjected to radiotherapy on the display;
   (c) means for developing contour lines indicative of isodoses of radiotherapy dose applied to the anatomical feature, and for superimposing said contour lines on the visual representation of the anatomical feature on the display means wherein the contour lines extend beyond the visual representation of the anatomical feature, said means including processing means for processing a plurality of weighting factors; and
   (d) means for developing a raster image configured for being superimposed over the visual representation of the anatomical feature and the contour lines of the isodose for selectively masking the contour lines of the isodose prior to undergoing a therapy session.

9. The system of claim 8, further comprising input means for selectively changing the weighting factors to thereby change the contour lines of the isodose.

10. The system of claim 8, wherein the means for developing a raster image comprises, more specifically, means for developing a raster image configured to mask all contour lines extending beyond the visual representation of the anatomical feature.

11. A method for displaying, on a display, an accurate model of isodoses used in Boron Neutron Capture Therapy (BNCT) planning, the method comprising:
   (a) obtaining a plurality of weighting values for at least one component of BNCT radiotherapy;
   (b) processing a plurality of weighting values, a patient image, beam geometries, and air spaces there between to determine at least one BNCT dose;
   (c) deriving isodoses from the at least one BNCT dose;
   (d) displaying contour lines to represent the derived isodoses, the contour lines extending through the entire treatment volume;

(e) generating a raster image for selectively masking out areas of unwanted isodose contour lines; and (f) selectively masking out areas of unwanted isodose contour lines prior to undergoing the BNCT session.

12. The method of claim 9, wherein the method comprises, more specifically, entering the weighting values into the computer via a radiation transport module.

13. The method of claim 11 for displaying an accurate model of isodoses wherein computing at least one BNCT dose from the plurality of weighting values comprises processing the weighting values with a processor programmed to compute at least one BNCT dose based on the entire treatment volume.

14. The method of claim 11 for displaying an accurate model of isodoses wherein displaying contour lines to represent the derived isodoses comprises processing the derived isodoses with a processor programmed to display the isodose contour lines based on the derived isodoses.

15. The method of claim 11 for displaying an accurate model of isodoses wherein providing a user with a raster image for masking out areas of unwanted isodose contour lines comprises generating the raster image with a processor programmed to generate a raster image that corresponds to the patient image on the display, the patient image showing anatomical features of a patient to be treated.

16. A system for displaying an accurate model of isodoses used in Boron Neutron Capture Therapy (BNCT) radiotherapy planning, the system comprising:

(a) a means for generating signals to form an isodose image, a raster image and a patient image on a display, the display having at least one graphical user interface for showing the isodose image, the raster image and the patient image;

(b) said isodose image being computed for the entire treatment volume of an anatomical feature of a patient, the isodose image having contour lines that extend over the patient image and the raster image;

(c) said raster image providing a means for masking out unwanted contour lines of the isodose image; and (d) said display having means for providing an accurate image of the computed isodoses, prior to undergoing a therapy session by a patient, the means for providing an accurate image of the computed isodoses causing the display to show only the desired contour lines of the isodose image superimposed over the patient image, the raster image masking out the unwanted contour lines.

17. A system for displaying an accurate model of isodoses used in Boron Neutron Capture Therapy (BNCT) radiotherapy planning, the system comprising:

a means for generating signals to form an isodose image, a raster image and a patient image on a display, the display having at least one graphical user interface for showing the isodose image, the raster image and the patient image;

said isodose image being computed for the entire treatment volume of an anatomical feature of a patient, the isodose image having contour lines that extend over the patient image and the raster image;

said raster image providing a means for masking out unwanted contour lines of the isodose image; and said display having means for providing an accurate image of the computed isodoses, the means for providing an accurate image of the computed isodoses causing the display to show only the desired contour lines of the isodose image superimposed over the patient image, the raster image masking out the unwanted contour lines.

18. The system of claim 16 wherein the display for the isodose image, the raster image, and the patient image comprises a computer screen.

19. The system of claim 16 wherein the isodose image computed for the entire treatment volume of an anatomical feature of a patient comprises isodose image contours that extend into air regions surrounding the anatomical features of the patient.

20. The system of claim 16 wherein the means for masking out unwanted contour lines of the isodose image comprises a general purpose computer programmed to illuminate the display only in areas covered by the raster image.

21. The system of claim 16 wherein the means for providing an accurate image of the computed isodoses comprises a general purpose computer programmed to overlap images on a computer screen.

* * * * *